US009675698B2

(12) United States Patent
Masini-Eteve et al.

(10) Patent No.: US 9,675,698 B2
(45) Date of Patent: *Jun. 13, 2017

(54) PHARMACEUTICAL COMPOSITION IN THE FORM OF A GEL OR A SOLUTION BASED ON DIHYDROTESTOSTERONE, PROCESS FOR PREPARING IT AND USES THEREOF

(75) Inventors: Valerie Masini-Eteve, Bourg-la-Reine (FR); Brigitte Taravella, Paris (FR)

(73) Assignee: BESINS HEALTHCARE LUXEMBOURG SARL, Luxembourg (LU)

( * ) Notice: Subject to any disclaimer, the term of this patent is extended or adjusted under 35 U.S.C. 154(b) by 760 days.

This patent is subject to a terminal disclaimer.

(21) Appl. No.: 13/317,113

(22) Filed: Oct. 11, 2011

(65) Prior Publication Data
US 2012/0157423 A1 Jun. 21, 2012

Related U.S. Application Data

(63) Continuation of application No. 10/456,868, filed on Jun. 6, 2003, now abandoned, which is a continuation-in-part of application No. 10/099,725, filed on Mar. 15, 2002, now abandoned.

(30) Foreign Application Priority Data

Dec. 7, 2001 (EP) ..................................... 01403166

(51) Int. Cl.
*A01N 45/00* (2006.01)
*A61K 31/56* (2006.01)
*A61K 47/14* (2017.01)
*A61K 9/00* (2006.01)
*A61K 31/565* (2006.01)
*A61K 47/10* (2017.01)
*A61K 47/18* (2017.01)
*A61K 47/32* (2006.01)

(52) U.S. Cl.
CPC ............ *A61K 47/14* (2013.01); *A61K 9/0014* (2013.01); *A61K 31/565* (2013.01); *A61K 47/10* (2013.01); *A61K 47/18* (2013.01); *A61K 47/32* (2013.01)

(58) Field of Classification Search
CPC .... A61K 47/17; A61K 9/0014; A61K 31/565; A61K 47/10; A61K 47/18; A61K 4/32
USPC ......................................................... 514/170
See application file for complete search history.

(56) References Cited

U.S. PATENT DOCUMENTS

| 5,152,997 | A | | 10/1992 | Ebert et al. |
| 5,208,013 | A | | 5/1993 | Klein |
| 5,589,498 | A | | 12/1996 | Mohr et al. |
| 5,613,958 | A | * | 3/1997 | Kochinke et al. ............ 604/307 |
| 5,648,350 | A | | 7/1997 | De Lignieres et al. |
| 5,844,103 | A | | 12/1998 | Au et al. |
| 5,863,560 | A | | 1/1999 | Osborne |
| 5,922,314 | A | | 7/1999 | Hoang et al. |
| 5,981,542 | A | | 11/1999 | Bigg et al. |
| 6,231,875 | B1 | | 5/2001 | Sun et al. |
| 2001/0036483 | A1 | | 11/2001 | Luo et al. |
| 2003/0027804 | A1 | * | 2/2003 | van der Hoop ............... 514/177 |

FOREIGN PATENT DOCUMENTS

FR 2 519 252 1/1982
WO WO 97/41865 4/1997

OTHER PUBLICATIONS

Solvay Pharmaceuticals; AndroGel 1% Internet, [Online} Sep. 2001, pp. 1-2.
Biam; "Andractim 2.5% Gel pour application locale" Internet, [Online] Nov. 30, 2000, pp. 1-4.
Kim M K et al.; "Skin permeation of testosterone and its easier derivatives in rats." Journal of Pharmacy and Pharmacology; Apr. 2000; 52 (4) 369-75.
Santus G C et al. "Transdermal enhancer patent literature" Journal of Controlled Release, Elsevier Science Publishers B. V. Amsterdam, NL, vol. 25, No. 1 / 2 , May 27, 1993, pp. 1-20.
Shaneyfelt et al., "Hormonal Predictors of Prostate Cancer: A Meta-Analysis," *Journal of Clinical Onocology*, vol. 18, No. 4, pp. 847-853, 2000.
Ly et al., "A Double-Blind, Placebo-Controlled, Randomized Clinical Trial of Transdermal Dihydrotestosterone Gel on Muscular Strength, Mobility, and Quality of Life in Older Men with Partial Androgen Deficiency," *The Journal of Clinical Endrocrinology & Metabolism*, vol. 86, No. 9, pp. 4078-4088, 2001.
Office Action issued on Jan. 29, 2003 by the Examiner in U.S. Appl. No. 10/099,725 (US 2003/0087885).
Office Action issued on Oct. 1, 2002 by the Examiner in U.S. Appl. No. 10/099,725 (US 2003/0087885).
European Search Report issued on Apr. 25, 2002 in application No. EP 01 40 3166 (corresponding to US 2003/0087885).
Barry, "Breaching the skin's barrier to drugs," Nature Biotechnology, vol. 22, pp. 165-167, 2004.
Wang et al., "Comparative Pharmacokinetics of Three Doses of Percutaneous Dihydrotestosterone Gel in Healthy Elderly Men: A Clinical Research Center Study," The Journal of Clinical Endocrinology & Metabolism, vol. 83, No. 8, 1998.
Office Action issued on Apr. 12, 2011 by the Examiner in U.S. Appl. No. 10/456,868 (US 2004-0072810).
Office Action issued on Oct. 27, 2010 by the Examiner in U.S. Appl. No. 10/456,868 (US 2004-0072810).
Office Action issued on May 11, 2010 by the Examiner in U.S. Appl. No. 10/456,868 (US 2004-0072810).
Office Action issued on Aug. 5, 2009 by the Examiner in U.S. Appl. No. 10/456,868 (US 2004-0072810).
Office Action issued on Jun. 28, 2006 by the Examiner in U.S. Appl. No. 10/456,868 (US 2004-0072810).
Office Action issued on Jan. 12, 2006 by the Examiner in U.S. Appl. No. 10/456,868 (US 2004-0072810).

* cited by examiner

Primary Examiner — Layla Soroush
(74) Attorney, Agent, or Firm — Foley & Lardner LLP

(57) ABSTRACT

The present invention relates to a pharmaceutical composition in the form of a hydro-alcoholic gel or a solution for transdermal application, comprising:
   from about 0.2% to about 1.5% of dihydrotestosterone; and from about 0.2 to about 3% of isopropyl myristate.

15 Claims, No Drawings

PHARMACEUTICAL COMPOSITION IN THE FORM OF A GEL OR A SOLUTION BASED ON DIHYDROTESTOSTERONE, PROCESS FOR PREPARING IT AND USES THEREOF

CROSS REFERENCE TO RELATED APPLICATION

This application is a continuation of U.S. patent application Ser. No. 10/456,868, filed on Jun. 6, 2003, which is a continuation-in-part of U.S. patent application Ser. No. 10/099,725, filed on Mar. 15, 2002.

The present invention relates to a pharmaceutical composition in the form of a gel or a solution based on dihydrotestosterone (DHT). The invention also relates to processes for preparing these formulations, as well as to their uses.

DHT is a metabolite of testosterone. In the sexual organs such as the prostate and the seminal vesicles, testosterone is reduced to DHT by the enzyme 5-α reductase.

During andropause (or "male menopause" or "partial deficiency of ageing male"), the secretion of androgens decreases and may, in certain cases, lead to pathological disorders. In particular, a change in protein synthesis and in the enzymatic activities of the target tissues is observed. Testosterone production and transportation become anomalous, as does its metabolism by the target tissues. These anomalies are typical of hypogonadism of the ageing male, but remain, to a large extent, undetected in the plasmatic assays usually performed.

Thus, in an andropausal ageing male, testosterone is secreted in reduced amounts and, very importantly, is insufficiently metabolized into DHT by the target tissues, as a result of a deficiency in 5-α-reductase. This is reflected by a reduction in androgenic activity. On the other hand, the aromatase enzymatic activity increases uniformly with age in the majority of men, thus maintaining oestradiol levels in the blood despite the fall in testosterone. The importance of these changes in intra-tissular activity is demonstrated by an increase in the level of SHBG (Serum Hormone Binding Globulin).

DHT is among the hormones required for the development of the male genital organs (penis, scrotum, prostate, seminal vesicles). It also plays a role in the development of male secondary sexual characteristics, including pilosity, the development of musculature, the deepening of the voice and the appearance of libido. It has an anabolic action on the skeleton and a stimulating action on the haematopoietic marrow at high doses.

DHT is prescribed in men as a systemic treatment for general androgenic deficiencies occurring as a result of permanent hypogonadism of testicular or hypophyseal origin, or of functional hypogonadism, usually due to surgical interventions, multiple injuries, burns, or intense and sustained physical or psychological constraints.

DHT is also used as a local treatment in men in the case of gynaecomasty and balano-preputial sclero-atrophic lichen. It may also be prescribed in women in the case of vulval sclero-atrophic lichen.

Treatments using DHT in the form of a gel are generally administered once a day, either in the morning or in the evening, by spreading the gel liberally over a large surface of the skin: arms, shoulders, chest, abdomen or thighs, and then leaving it to dry for about five minutes before putting any clothing on the application area.

As regards the composition in the form of a solution, it may be applied in the form of a spray which would be readily vaporized over a large surface area of skin.

This type of application involves a relatively large amount of gel or solution, namely 5 to 10 grams per day, depending on the therapeutic indication. The individual dosage must also take account of the intensity of the androgen deficiency to be compensated for and also the tolerance of the individual subject to the dose applied.

It would thus be advantageous to be able to reduce the amount of gel or of solution to be applied and thus to reduce the application surface. This may also lead to an improvement in the patient's compliance with the treatment and to a reduction in the risk of cross-contamination between two individuals.

The secondary effects of DHT are far from being benign: irritability, psychomotor excitation, weight gain, seborrhoea and acne, in men; there is also the problem of virilization in women.

In addition, as for any hormone, it is in the patients' interest to be able to reduce the dosage to the minimum effective amount, so as to reduce the adverse effects.

The Assignee of the present patent application has already developed and marketed a DHT-based gel in Europe under the name ANDRACTIM®. This formulation has been patented as FR 2 519 252. The DHT concentration in this formulation is 2.5%, but no percutaneous absorption promoter is contained therein.

The Applicants have since found that the gel formulation according to patent FR 2 519 252 containing DHT in an amount of 2.5 g per 100 g of gel suffers from other drawbacks such as a physicochemical instability which results in the appearance of crystals in the gel during storage at room temperature.

The Assignee of the present application is also the proprietor of a patent EP 0 700 293 relating to the use of DHT in androgen therapy, and more particularly regarding the favourable effects of DHT on prostate hyperplasia.

In EP 0 700 293 it is simply indicated that an aqueous-alcoholic gel having a DHT content of from 0.5% to 3.5% may be used in order to obtain the favourable effects of DHT on prostate hyperplasia. This being said, the patent gives no additional information whatsoever regarding the constituents of such a gel, its method of manufacture, or its efficacy. There is absolutely no mention made in this patent of a percutaneous absorption promoter being used in combination with DHT.

Thus, neither FR 2 519 252 nor EP 0 700 293 ever envisioned the addition of a percutaneous absorption promoter to the DHT topical formulations disclosed therein.

In an article published in 1998, Wang et al. (J. of Clin. Endo. & Metab., vol. 83, 1988; p. 2749-2757) conducted tests using an earlier DHT gel formulation of the Applicants. This publication only discloses the general ingredients of said gel, without providing any information whatsoever on the specific quantities of each ingredient, except with respect to DHT which is cited as being present in an amount of 0.7%.

Since the publication of the Wang article, the Applicants have conducted further research studies on the gel/solution formulations containing DHT and have optimized the DHT gel/solution formulation with respect to the ingredients and their specific percent ranges contained therein.

The Applicants have thus sought to develop a novel, stable DHT-based formulation which allows the concentration of DHT to be applied to the skin to be reduced significantly with respect to the previously commercialized ANDRACTIM® product, while at the same time maintaining highly satisfactory levels of skin absorption and efficiency of the active ingredient This results in an economic advantage, due to the reduction in the concentration of DHT used in the formulations, as well as the abovementioned therapeutic advantages and further advantages in terms of the physicochemical stability of the formulation.

The Applicants have, to their credit, developed a DHT-based pharmaceutical form for transdermal application, which can be used for the treatment of the ageing male. In fact, the use of DHT in the treatment of hypogonadism in the ageing male presenting an abnormally high level of SHBG (sign of an intra-tissular dysfunction) is more advantageous than treatment with testosterone.

In these men, the activity of the enzyme 5α-reductase is reduced. As a result, testosterone is poorly reduced to DHT, the active metabolite. It is thus more advantageous to treat ageing males directly using the naturally active androgen: DHT rather than testosterone.

It is important to note that the estrogenic effects of testosterone are not manifested on the bone or on the majority of the other targets. Furthermore, testosterone is potentially harmful to the prostate since the increase in testosteronaemia is suspected of elevating the risk of cancer in the ageing male (Ly L. P. et al., J. Clin. Endocrinol Metab., 2001; 86: 4078-4088; Wang C. et al., J. Clin. Endocrinol Metab., 1998; 83: 2749-2757; Shaneyfelt T. et al., J. Clin. Oncol. 2000; 18: 847-853).

Thus, the invention relates to a pharmaceutical composition in the form of a gel or a solution, characterized in that it contains dihydrotestosterone and also at least one percutaneous absorption promoter.

The expression "percutaneous absorption promoter" means any molecule promoting the reversible diffusion of an active principle through the skin reversibly, and any solubilizing agent promoting the partition of the active principle from the vehicle to the horny layer of the epidermis.

International patent application WO 92/07590 explains, however, that it is not at all possible to predict the behaviour of an active substance as regards its passage across the transdermal barrier and furthermore that a percutaneous absorption promoter which is effective with respect to a given active substance is not necessarily effective with another active substance.

According to one advantageous embodiment of the pharmaceutical composition according to the invention, the DHT content is less than 1.5%, preferably from 0.2% to 1.5%, more preferably from 0.5% to 1.2%, even more preferably from 0.7 to 1.0%, and most preferably is about 0.7%, this percentage being expressed by weight per 100 g of formulation.

In order to achieve an effective concentration of active principle without, however, covering an excessively large area of skin, the active principle is combined with a percutaneous absorption promoter.

This absorption promoter is chosen so as to improve the systemic absorption of the DHT and thus to obtain the desired effects by means of an acceptable cutaneous coverage, that is to say less than 15 µg of DHT per cm$^2$, preferably 10 µg of DHT per cm$^2$ and even more preferably 7 µg of DHT per cm$^2$.

This percutaneous absorption promoter will be selected from substances that are compatible with the chosen non-aqueous solvent. Preferably, it will be chosen from the compounds mentioned below which have a necessary degree of solubility in the solvent under consideration and are non-irritant, non-allergenic and non-toxic. The chosen promoter will also have to be compatible with all of the components of the formulation selected and must be chemically and physically stable.

As examples of promoters that may be used, alone or in combination, in the pharmaceutical composition according to the invention and which have shown good properties in promoting the cutaneous absorption of active substances, mention may be made of: aliphatic fatty acid esters such as isopropyl myristate; fatty acids such as oleic acid; alcohols or polyols such as ethanol, propylene glycol and polyethylene glycols; components of essential oils and terpine derivatives (such as eugenol, geraniol, nerol, eucalyptol or menthol); surfactants; moisturizers such as glycerol, urea; keratolytic agents such as α-hydroxy acids.

Isopropyl myristate represents the preferred absorption promoter for the pharmaceutical composition according to the invention. Isopropyl myristate is introduced into the composition of the invention in a proportion of from about 0.2% to about 3%, preferably from about 0.4% to about 2%, more preferably from about 0.5% to about 1.0% and even more preferably of about 0.7%, these percentages being expressed by weight per 100 g of formulation.

The pharmaceutical composition according to the invention also contains a solvent. The solvent used is a non-aqueous solvent capable of dissolving DHT and the absorption promoter. It will be chosen from compounds with a low boiling point, i.e. less than 100° C. at atmospheric pressure, so that it can evaporate rapidly on contact with the skin. Such solvents may be selected, alone or in combination, from volatile compounds such as ethanol, isopropanol or ethyl acetate; preferably ethanol and/or isopropanol. However, ethanol represents a preferred solvent according to the invention. Ethanol contributes with efficiency towards the transcutaneous passage of the active principle by evaporating rapidly on contact with the skin and by allowing a local saturation of DHT, which favours percutaneous diffusion from the vehicle to the epidermis and the dermis. The absolute ethanol content is from about 50% to about 75%, preferably from about 60% to about 70%, more preferably from about 63 to about 67% and most preferably of about 66%, these percentages being expressed by weight relative to 100 g of formulation.

The pharmaceutical composition according to the invention may also comprise an aqueous vehicle. The aqueous vehicle makes it possible to dissolve the hydrophilic molecules contained in the formulation and also promotes the diffusion of the lipophilic molecules of the formulation towards the horny layer. It may also act as a pH regulator.

The aqueous vehicle may be a selected buffer or may simply be purified water. The aqueous vehicle is at a content of between about 15% to about 45%, preferably from about 20% to about 40%, more preferably from about 25 to about 35% and most preferably of about 27%, these percentages being expressed by weight relative to 100 g of formulation. The aqueous vehicle content is always adjusted during the manufacturing process in order to reach the weight of 100 for 100 g of the composition.

Purified water is the preferred aqueous vehicle used in the composition according to the present invention.

The pharmaceutical composition according to the invention may, in certain cases, also comprise a gelling agent. Advantageously, and depending on the type of gelling agent used, it has a content of from about 0.2% to about 2% of a gelling agent, preferably from about 0.3% to about 1%, more preferably from about 0.4% to about 0.8%, and most preferably of about 0.5%, these percentages being expressed on a weight basis per 100 g of pharmaceutical composition.

The gelling agent is preferably selected from the group consisting of carbomers and cellulose derivatives. More particularly, the gelling agents may be selected from the following compounds:

Carbomers or polyacrylic acids such as carbopol 980 or 940 NF, 981 or 941 NF, 1382 or 1382 NF, 5984, 2984 or 934 NF, Pemulen TR1 NF or TR2 NF, Ultrez, Synthalen CR, and the like;

Cellulose derivatives such as ethyl cellulose, hydroxypropyl cellulose, hydroxyethyl cellulose, hydroxypropyl methyl cellulose (HPMC), carboxymethyl cellulose (CMC), and the like.

These gelling agents make it possible to increase the viscosity of the formulations according to the invention, but may also act as solubilizing agents.

Hydroxypropylcellulose and Carbopol® 980 (carboxyvinyl polymer grade 980, polymerized in an ethyl acetate/cyclohexane system) are particularly preferred in the context of the present invention.

The gelling agent is selected taking into account the pH of the composition according to the invention, the desired viscosity and the absorption promoter in the composition, and specifically in the case of the present invention, the isopropyl myristate content.

According to another advantageous embodiment of the pharmaceutical composition according to the invention when it is in the form of a gel and in the presence of certain types of gelling agent, preferably those containing carboxylic functions (—COOH) such as carbomers, it may contain a neutralizer. The neutralizer/gelling agent ratio is between about 3/1 and about 0.5/1, preferably from about 2/1 to about 0.5/1, more preferably from about 1.5/1 to about 0.5/1 and most preferably of about 1/1.

This neutralizer is chosen such that it forms soluble polymer salts in the hydroalcoholic vehicle. The neutralizer is also chosen so as to be able to achieve optimum swelling of the polymer chains during the neutralization of the charges and the formation of polymer salts.

According to the invention, triethanolamine is preferably used as neutralizer in the presence of Carbopol® 980. It also allows an optimum viscosity to be achieved in the pharmaceutical composition according to the invention. In this case, the preferred neutralizer/gelling agent ratio is 1/1.

Other neutralizers, for instance sodium hydroxide, ammonium hydroxide, potassium hydroxide, arginine, aminomethylpropanol or tromethamine, may be used in the pharmaceutical composition according to the invention. The neutralizer is chosen as a function of the type of gelling agent used, in a manner that is known to the person skilled in the art.

The invention also relates to a process for preparing a pharmaceutical composition in the form of a gel or a solution according to the invention. This process comprises the following successive steps:

DHT is dissolved, with stirring, in a mixture of solvents and absorption promoter;

water is added, with stirring, to the mixture obtained.

In the case of a gel, the following additional steps are performed:

a gelling agent, such as carbopol, is then added to the mixture, with stirring;

optionally, a neutralizer such as triethanolamine is added to the mixture, with stirring.

The invention also relates to the use of the gel or the solution according to the invention for the preparation of a medicinal product for transdermal application for the treatment of a physiological condition associated with an androgen deficiency.

Examples of such physiological conditions which may be mentioned include:

in adults: permanent or functional hypogonadism with or without sexual dysfunction and/or with depression in men, hyperplasia of the prostate, gynaecomasty, balano-preputial sclero-atrophic lichen in men and vulval and perianal sclero-atrophic lichen in women;

in paediatrics: micropenis.

The pharmaceutical composition according to the invention may also comprise an oestrogen, preferably selected from the group consisting of 17β-oestradiol, oestrone, 17α-ethynyl-oestradiol and oestradiol valerate, and even more preferably 17β-oestradiol at a dose bioequivalent to 0.5 mg of 17β-oestradiol administered orally.

DHT has an anti-gonadotropic and thus anti-oestrogen effect. Although it has not been proven that oestrogens play a positive role on the bones, it may be recommended, as a preventive measure, to combine the administration of oestrogen with that of DHT in men having insufficient levels of oestradiol in the blood in order to compensate for this loss and to allow them to regain an acceptable physiological level.

The invention will be understood more clearly with the aid of the non-limiting examples described below.

EXAMPLE I: PHARMACEUTICAL COMPOSITION IN THE FORM OF A GEL ACCORDING TO THE INVENTION

A gel according to the invention having the formulation below was prepared by the Applicants. The amounts are given per 100 g of gel:

| | |
|---|---|
| Dihydrotestosterone | 0.7 g |
| Ethanol 95° | 71.0 g |
| Carbopol 980 | 0.5 g |
| Isopropyl myristate | 0.7 g |
| Triethanolamine | 0.5 g |
| Purified water qs | 100.0 g |

EXAMPLE II: PHARMACEUTICAL COMPOSITION IN THE FORM OF A SOLUTION ACCORDING TO THE INVENTION

A solution according to the invention having the formulation below was prepared by the Applicants. The amounts are given per 100 g of solution:

| | |
|---|---|
| Dihydrotestosterone | 0.7 g |
| Ethanol 95° | 71.0 g |
| Isopropyl myristate | 0.7 g |
| Purified water qs | 100.0 g |

EXAMPLE III: PROCESS FOR PREPARING A GEL ACCORDING TO THE INVENTION

The manufacture of a DHT-based gel according to the invention is carried out as follows: for a batch of 70 kg containing 0.7% DHT, the following process is performed:

49 700 g of 95% ethanol are placed, under a vacuum of 800 mbar without stirring, in the tank of a mixer of Koruma™ type. Next, 490 g of isopropyl myristate are added via the top of the tank. Finally, 490 g of DHT are added via the top of the tank.

The above ingredients are mixed for 10 minutes, turbine at 2 000 rpm, doctor blade at 40 rpm, until the DHT is completely dissolved.

18 620 g of purified water are added under a vacuum of 800 mbar and mixing is carried out using a doctor blade at 40 rpm.

350 g of Carbopol® 980 are added under a vacuum of 800 mbar. Mixing is carried out at 2 000 rpm. The vacuum is broken. Mixing is carried out for 10 minutes, turbine at 2 000 rpm, doctor blade at 40 rpm.

Triethanolamine is added via the top of the tank. Mixing is carried out for 3 minutes, turbine at 2 000 rpm, doctor blade at 40 rpm.

The mixer is placed under a vacuum of 120 mbar for 2 to 3 minutes. Next, the vacuum is broken and stirring is then carried out for 20 minutes with the doctor blade at 40 rpm.

EXAMPLE IV: PROCESS FOR PREPARING A SOLUTION ACCORDING TO THE INVENTION

Manufacture of a DHT-based solution according to the invention is carried out as follows:

For a batch of 70 kg containing 0.7% DHT, the process is performed in the following manner:

49 700 g of 95% ethanol are added, under a vacuum of 800 mbar without stirring, to the tank of a mixer of Koruma™ type. Next, 490 g of isopropyl myristate are added via the top of the tank. Finally, 490 g of DHT are added via the top of the tank.

Mixing is carried out for 10 minutes, turbine at 2 000 rpm, doctor blade at 40 rpm, until the DHT has completely dissolved.

19 320 g of purified water are added under a vacuum of 800 mbar, doctor blade at 40 rpm.

The mixer is placed under a vacuum of 120 mbar for 2 to 3 minutes. Next, the vacuum is broken and stirring is then carried out for 20 minutes with the doctor blade at 40 rpm.

EXAMPLE V: PHARMACOKINETIC STUDIES IN VITRO AND IN VIVO

In Vitro Studies

Comparative studies of percutaneous absorption on human abdominal skin between the formulation Andractim® containing 2.5% DHT and the 0.7% gel formulation described according to the invention were performed on Franz cells.

The formulations were applied at a dose of about 13 μg of DHT per cm$^2$ onto an area of 1.77 cm$^2$ of skin.

The results show that the levels of DHT absorbed are comparable between the two formulations: 0.47 μg and 0.32 μg of DHT absorbed, respectively, for the 0.7% gel and the 2.5% gel.

In Vivo Study:

A phase I pharmacokinetic study was performed in order to compare the pharmacokinetic parameters of the formulation Andractim® containing 2.5% DHT and the formulation according to the invention, containing 0.7% DHT, after repeated percutaneous administration. This study was an open cross-over study on 18 patients without placebo. 5 g of Andractim® 2.5% gel (i.e. 125 mg of DHT) or 5 g of gel according to the invention at 0.7% (i.e. 35 mg of DHT) were administered once a day for 7 days.

The pharmacokinetic parameters of each of the formulations administered were evaluated and are as follows.

The average plasmatic concentrations of DHT observed as a function of the formulation used are summarized in the Table 1 on days 1, 5 and 8 following the start of the study (day 0).

TABLE 1

Average plasmatic concentrations of DHT after administration of the Andractim ® formulation containing 2.5% DHT or of the formulation according to the invention, containing 0.7% DHT, after repeated percutaneous administration (open cross-over study on 18 patients without placebo. 5 g of Andractim ® 2.5% gel (i.e. 125 mg of DHT) or 5 g of gel according to the invention at 0.7% (i.e. 35 mg of DHT) were administered once a day for 7 days).

|  | Mean ± standard deviation (ng/mL) | | |
| --- | --- | --- | --- |
|  | Day 1 | Day 5 | Day 8 |
| 2.5% Andractim | 0.597 ± 0.165 | 4.31 ± 2.06 | 3.62 ± 1.83 |
| 0.7% DHT gel | 0.621 ± 0.217 | 3.83 ± 2.02 | 3.38 ± 1.30 |

The AUCs (areas under the curve) calculated between 0 and 24 hours on day 7 are equal to 85.4 ng·h/mL (35% CV) after treatment with Andractim® 2.5% and 102 ng·h/mL (33% CV) after treatment with the DHT gel formulation according to the invention at 0.7%.

The average plasmatic concentrations of DHT on day 7 (from 0 to 24 hours) are equal to 3.98±1.32 ng/mL after treatment with Andractim® 2.5% and 4.60±1.51 ng/mL after treatment with the DHT gel formulation according to the invention at 0.7%.

The results obtained in vivo shows that the two treatments (Andractim® 2.5% and the DHT gel formulation according to the invention at 0.7%) show relatively similar pharmacokinetics.

The statistical tests performed in accordance with the international regulations in force for medicinal products intended to be administered to humans demonstrate that the bioequivalence is not significant between the two treatments and that the 0.7% DHT formulation according to the invention is super-bioavailable relative to Andractim® 2.5%.

EXAMPLE VI: IN VITRO PERCUTANEOUS ABSORPTION ASSAY ON HUMAN SKIN OF DIHYDROTESTOSTERONE INCORPORATED IN HYDROALCOHOLIC GELS OR SOLUTIONS: OPTIMIZATION OF DHT CONCENTRATION AND ISOPROPYL MYRISTATE CONCENTRATION

In vitro percutaneous absorption is studied quantitatively with human skin biopsies placed in the FRANZ diffusion cells permitting contact of a survival liquid with the dermis in which the substance absorbed is measured.

A skin biopsy is maintained horizontally between two parts of the cell, thus delimiting two separate compartments: one, epidermic, consists in a glass cell cap of precise surface (1.77 cm$^2$), placed on the upper side of the skin; the other, dermic, on the lower side of the tegument, comprises a reservoir of fixed volume (around 6.5 ml) supplied with a lateral collection port.

The two elements are held in place with a clamp. The dermic compartment is filled with a survival liquid constituted by a solution of sodium chloride at 9 g/l and bovine serum albumin at 15 g/l. This liquid is periodically totally extracted throughout the assay and is replaced by fresh survival liquid by the lateral collection port.

A double water circulation jacket surrounds the lower part of the cell in order to maintain the skin temperature at 32±1° C.

To ensure the homogeneity of the temperature and the content in the receptor phase, a stirring rod is placed in the dermic compartment and each cell is placed on a magnetic stirrer.

The upper part, or epidermic compartment, is open towards the exterior, thus exposing the surface of the skin to the surrounding air.

Human abdominal skins are obtained from plastic surgery procedures. The biopsies are stored no more than 12 months at −20° C. before being used. After thawing, the skin is dermatomed at about 500 μM (air dermatome commercialized by Zimmer, France).

The skin is fitted on the cells the day before the application of the preparations.

Various formulations of DHT gel or solution are prepared using radiolabeled DHT.

5 alpha dihydro [1, 2, 4, 5, 6, 7-$^3$H] testosterone delivered in solution (1 mCi/ml, 37 MBq/ml) in toluene:ethanol (9:1) is obtained from Amersham Bioscience (Parc Technologique, France). The specific activity is of 108 Ci/mmol, i.e. 362 mCi/mg, for a molecular weight of 298 at this specific activity. The radiochemical purity of DHT is equal to 99.5%.

All other raw materials are provided by Laboratoires Besins-International (Montrouge, France). Dihydrotestosterone (DHT), Batch no 02065911. Ethanol 96, Batch no 03036490. Isopropyl myristate (IPM), Batch no 02106193. Carbopol 980NF, Batch no 02075967. Triethanolamine (TEA=trolamine), Batch no 03016406.

Radioactive Gel or Solution Formulations are Prepared as Follows:

Solutions 180 mg are prepared as follows:
- 18 μl (18 μCi) of the solution of $^3$H-DHT is evaporated at room temperature under a gentle stream of air in a glass flask.
- Following evaporation, appropriate weight of a solution containing DHT in alcohol with IPM is added in the flask and the flask is shaken with a vortex in order to obtain a homogenous radioactive solution. Then, an appropriate amount of water is added and the solution is again shaken.
- Radioactive concentration of the solutions is designed to have approximately 0.5 μCi of DHT for an administered dose of solution of about 4.4 mg (5 μl) per Franz cell of 1.77 cm$^2$.

Gels

500 μl are prepared as follows:
- 50 μl (50 μCi) of the solution of $^3$H-DHT is evaporated at room temperature under a gentle stream of air in a glass flask.
- Following evaporation, 500 μl of the gel is introduced in the glass flask and vigorously shaken many times in order to obtain a homogenous radioactive gel. Air bubbles introduced during agitation are removed by centrifugation at 1000 g for 5 minutes at 20° C.
- Radioactive concentration of the gel is designed to have approximately 0.5 μCi of DHT for an administered dose of gel of 4.4 mg (5 μl) per Franz cell of 1.77 cm$^2$.
- The homogeneity of radioactivity is determined by the counting level of 9 exactly weighed samples for each preparation (standard).

5 μl of the formulations are applied over the surface of the epidermis delimited by the cone glass (1.77 cm$^2$). The quantity of the composition according to the invention applied by cm$^2$ of the epidermis corresponds to the real quantity applied by a patient under clinical use.

During the experiment, the survival liquid is completely removed at 2, 4, 6, 8 and 24 hours through the lateral collection port and the dermal compartment is refilled with fresh solution.

At the end of the test (24 hours), the residual drug remaining at the surface of the skin is removed by cyclic washing the surface with 200 μl of different solvents (Cetavlon™ alcoholic/water (10/90 v/v), water). Cetavlon™ alcoholic is sold by Laboratories Zeneca Pharma and corresponds to cetrimide 0.5% in ethanolic solution 60°. The application area is then wiped with a cotton wool stick. All the washing solvents, the cotton wool stick, the upper part of the cell are introduced in a flask with 30 ml ethanol 95° exactly weighed in order to extract the residual radioactivity, and incubated overnight at +4° C.

The skin is separated from the lower part of the cell, and the epidermis and dermis are then separated using a scalpel. The epidermis and dermis are digested for extraction of radioactivity, with respectively 1 ml and 3 ml of Soluene 350™ (PACKARD), for several hours at 60° C., then at room temperature.

The radioactivity contained in the samples obtained as previously described, is measured in its totality or in weighed aliquots using a scintillating liquid beta counter (PACKARD Tricarb 2900TR).

The evaluation is performed with Picofluor 40™ (PACKARD) for the standards (0.005 ml/5 ml Picofluor 40™), for the survival liquid (6.5 ml/15 ml Picofluor 40™) and for an exactly weighed aliquot of the ethanol solution containing the washing solvents (0.5 ml/5 ml Picofluor 40™).

For the epidermis and the dermis, after digestion, 15 ml of Hionic Fluor 30™ (PACKARD) are added.

The background of the counter is deducted from the counting rate of each sample in counts per minute (cpm). This rate of counting is then corrected with regard to the autoextinction using the method of external standard to obtain disintegrations per minute (dpm), which account for the true activity of each sample. For each scintillation mixture used, a specific autoextinction curve is established.

The results are expressed in quantities or in percentages of applied DHT, found in the different compartments. Applied quantities of DHT are determined from the counting level of diluted standards. Each result represents the mean value of 6 experimental determinations and is associated with its standard deviation. The intensity of absorption is obtained by calculating:

a) The quantity of DHT and the % of the dose absorbed in the survival liquid for each time, calculated as follows:

$$\% = (Qt/Qi) \times 100$$

where Qt represents absorbed amount at time t, and Qi applied quantity at time 0, b) The total quantity and corresponding % of the dose absorbed as a function of the time (cumulated values), c) The mean flux of diffusion between two times of dosing, expressed in ng/cm$^2$/hrs, d) The quantity and % of the administered dose which is found in the epidermis, in the dermis and in the washing solvents.

The validity of the test is checked by balancing the radioactivity which is found in the different samples (this summarisation should be comprised, for each test, between 85% and 115% of the applied dose).

The comparison of results is assessed by the Mann Whitney test (non parametric analysis for two non paired groups), with the Statview512+™ software (SAS Institute).

Different pharmaceutical compositions of gel or solution were tested for different contents (w/w) of isopropyl myristate (from 0 to 4%) or of dihydrotestosterone (from 0.7 to 1.5%). The ethanol content was determined taking into account the isopropyl myristate content and also its solubility limits in a hydroalcoholic medium. All the experiments were performed using as a reference a gel or a solution containing DHT at a content of 0.7% and isopropyl myristate at a content of 0.7%.

TABLE 2

Pharmaceutical composition according to the invention and their significant ($p < 0.05$) absorption promotion factors* determined by comparison with the composition containing 0.25% (w/w) of isopropyl myristate.

| Formulation number | 2 | 3 | 5 | 6 |
|---|---|---|---|---|
| Formulation Compositions | | | | |
| DHT | 0.7 | 0.7 | 0.7 | 0.7 |
| IMP | 0.45 | 0.70 | 1.00 | 2.00 |
| ETHANOL 96° | 65.0 | 71.0 | 70.9 | 74.8 |
| Carbopol 980 | 0.5 | 0.5 | 0.5 | — |
| Trietanolamine | 0.5 | 0.5 | 0.5 | — |
| Purified water | Qsf 100 | Qsf 100 | Qsf 100 | Qsf 100 |
| Absorption promotion factor | | | | |
| DHT inside the dermis | 1.62 | 1.75 | 2.11 | 2.95 |
| DHT absorbed + inside the dermis | 1.67 | 1.51 | 1.89 | 2.37 |

*The promotion factor is determined by the ratio of the absorption rate between two formulations.
Qsf: Quantity sufficient for The results obtained demonstrate that for a fixed DHT content, there is a significant increase ($p<0.005$) of the DHT content inside the dermis or of the DHT absorbed plus the DHT inside the dermis when the concentrations of isopropyl myristate are increased (see Table 2). This increase is proportional to the isopropyl myristate content of the pharmaceutical composition prepared according to the invention. For example, for a DHT content of 0.7% and for an isopropyl myristate content varying from 0.45% to 2.00%, the absorption factor increase inside the dermis from 1.62 to 2.95 by comparison with a composition containing 0.25% of isopropyl myristate.

TABLE 3

Pharmaceutical composition according to the invention and their significant ($p < 0.05$) absorption promotion factors* determined by comparison with the composition containing no isopropyl myristate.

| Formulation number | 2 | 3 |
|---|---|---|
| Formulation Compositions | | |
| DHT | 1.5 | 1.5 |
| IMP | 0.25 | 0.45 |
| ETHANOL 96° | 61.1 | 65.0 |
| Carbopol 980 | 0.5 | 0.5 |
| Trietanolamine | 0.5 | 0.5 |
| Purified water | Qsf 100 | Qsf 100 |
| Absorption promotion factor | | |
| DHT absorbed | 1.65 | 1.92 |
| DHT absorbed + inside the dermis | 1.40 | 2.00 |

*The promotion factor is determined by the ratio of the absorption rate between two formulations.
Qsf: Quantity sufficient for In the absence of isopropyl myristate (see Table 3), the amount of DHT absorbed or the DHT content inside the dermis is significantly lower ($p<0.005$) than in the presence of lower isopropyl myristate content. For example, for a DHT content of 1.5% and for an isopropyl myristate content of 0.25% and 0.45%, the relative absorption factors of the DHT absorbed and inside the dermis by comparison with a composition containing no isopropyl myristate are 1.40 and 2.00, respectively.

At high concentrations of isopropyl myristate and depending on the DHT content, results show there is no significant evolution of the DHT absorption rate and it seems that the dermis is saturated in DHT and it can no longer absorb and release the DHT. This "dead level" is achieved for an isopropyl myristate content of around 2.7% and around 2.0% for DHT contents of 0.7% and 1.5%, respectively.

What we claim is:

1. Pharmaceutical composition for the transdermal delivery of dihydrotestosterone for systemic absorption in the form of a gel or a solution, comprising from 0.2% to 1.5% dihydrotestosterone, from about 0.2% to about 3% isopropyl myristate, and from about 50% to about 75% ethanol, these percentages being expressed by weight based on the weight of the composition.

2. The pharmaceutical composition according to claim 1, wherein the dihydrotestosterone content is 0.7% by weight based on the weight of the composition.

3. The pharmaceutical composition according to claim 1, wherein the ethanol content is from about 60% to about 71% by weight based on the weight of the composition.

4. The pharmaceutical composition according to claim 1, wherein the isopropyl myristate content is from about 0.4% to about 2% by weight based on the weight of the composition.

5. The pharmaceutical composition according to claim 1, wherein the isopropyl myristate content is about 0.7% by weight based on the weight of the composition.

6. The pharmaceutical composition according to claim 1, further comprising a gelling agent at a content from 0.05% to 3% by weight based on the weight of the composition.

7. The pharmaceutical composition according to claim 6, wherein the gelling agent is selected from the group consisting of carbomers, cellulose derivatives, poloxamers, poloxamines, and mixtures thereof.

8. The pharmaceutical composition according to claim 7, wherein the gelling agent is a carbomer.

9. The pharmaceutical composition according to claim 6, wherein the gelling agent content is from 0.2% to 2% by weight based on the weight of the composition.

10. The pharmaceutical composition according to claim 6, further comprising a neutralizer.

11. The pharmaceutical composition according to claim 10, wherein the neutralizer is selected from the group consisting of triethanolamine, sodium hydroxide, ammonium hydroxide, potassium hydroxide, arginine, aminomethylpropanol, tromethamine, and mixtures thereof.

12. The pharmaceutical composition according to claim 10, wherein the neutralizer is triethanolamine.

13. The pharmaceutical composition according to claim 10, in which the neutralizer-gelling agent ratio is between 10/1 and 0.1/1.

14. The pharmaceutical composition according to claim 10, in which the neutralizer-gelling agent ratio is between 7/1 and 0.5/1.

15. A process for preparing a pharmaceutical composition according to claim 1, comprising:
   preparing a mixture of the ethanol, isopropyl myristate and dihydrotestosterone;
   optionally, adding a gelling agent to the mixture and mixing;

optionally, adding a neutralizer to the mixture and mixing; and recovering the pharmaceutical composition containing dihydrotestosterone.

* * * * *

UNITED STATES PATENT AND TRADEMARK OFFICE
CERTIFICATE OF CORRECTION

PATENT NO. : 9,675,698 B2  Page 1 of 1
APPLICATION NO. : 13/317113
DATED : June 13, 2017
INVENTOR(S) : Masini-Eteve et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 830 days.

Signed and Sealed this
Twenty-fifth Day of September, 2018

Andrei Iancu
*Director of the United States Patent and Trademark Office*